United States Patent
Townsend

(10) Patent No.: US 8,517,936 B1
(45) Date of Patent: Aug. 27, 2013

(54) EYELID LIFTING DEVICE

(76) Inventor: Darryl Townsend, Dade City, FL (US)

( * ) Notice: Subject to any disclaimer, the term of this patent is extended or adjusted under 35 U.S.C. 154(b) by 0 days.

(21) Appl. No.: 13/397,525

(22) Filed: Feb. 15, 2012

(51) Int. Cl.
*A61B 1/32* (2006.01)

(52) U.S. Cl.
USPC ........................................... 600/236

(58) Field of Classification Search
USPC ........... 602/44, 52, 54–58, 74; 604/304–308, 604/294–302
See application file for complete search history.

(56) References Cited

U.S. PATENT DOCUMENTS

| | | | | | |
|---|---|---|---|---|---|
| 2,018,517 | A | * | 10/1935 | Fetter | 606/215 |
| 3,699,958 | A | * | 10/1972 | Szucs | 604/304 |
| 4,733,659 | A | * | 3/1988 | Edenbaum et al. | 602/54 |
| 5,070,860 | A | * | 12/1991 | Grounauer | 600/236 |
| 5,116,675 | A | * | 5/1992 | Nash-Morgan | 428/343 |
| 5,183,060 | A | * | 2/1993 | Shito | 128/882 |
| 5,433,190 | A | * | 7/1995 | Sunalp | 600/236 |
| 5,611,333 | A | * | 3/1997 | Johnson | 128/200.24 |
| 7,067,710 | B1 | * | 6/2006 | Beaudry | 602/54 |
| 2010/0145156 | A1 | * | 6/2010 | Davis | 600/236 |

* cited by examiner

*Primary Examiner* — Mary Hoffman
(74) *Attorney, Agent, or Firm* — Edward P Dutkiewicz

(57) ABSTRACT

A eyelid lifting device, comprising an eyelid contacting member, and a forehead contacting member, and an elastomeric connecting member. The eyelid contacting member and the forehead contacting member each having an adhesive layer with a cover coupled thereto.

5 Claims, 2 Drawing Sheets

EYELID LIFTING DEVICE

BACKGROUND OF THE INVENTION

1. Rule 1.78(F) (1) Disclosure

The Applicant has not submitted a related pending or patented non-provisional application within two months of the filing date of this present application. The invention is made by a single inventor, so there are no other inventors to be disclosed. This application is not under assignment to any other person or entity at this time.

2. Field of the Invention

The present invention relates to a eyelid lifting device and more particularly pertains to a device for lifting a user's eyelid.

3. Description of the Prior Art

The use of adhesive devices is known in the prior art. More specifically, adhesive devices previously devised and utilized for the purpose of attaching and holding two anatomical structures are known to consist basically of familiar, expected, and obvious structural configurations, notwithstanding the myriad of designs encompassed by the crowded prior art which has been developed for the fulfillment of countless objectives and requirements.

While the prior art devices fulfill their respective, particular objectives and requirements, the prior art does not describe eyelid lifting device that allows a device for lifting a user's eyelid.

In this respect, the eyelid lifting device according to the present invention substantially departs from the conventional concepts and designs of the prior art, and in doing so provides an apparatus primarily developed for the purpose of lifting a user's eyelid in a simple and safe manner.

Therefore, it can be appreciated that there exists a continuing need for a new and improved eyelid lifting device which can be used for lifting a user's eyelid. In this regard, the present invention substantially fulfills this need.

SUMMARY OF THE INVENTION

In view of the foregoing disadvantages inherent in the known types of adhesive devices now present in the prior art, the present invention provides an improved eyelid lifting device. As such, the general purpose of the present invention, which will be described subsequently in greater detail, is to provide a new and improved eyelid lifting device which has all the advantages of the prior art and none of the disadvantages.

To attain this, the present invention essentially comprises an eyelid lifting device, comprising several components, in combination.

First there is an eyelid contacting member. The eyelid contacting member has a flexible fabric layer. The flexible fabric layer is in a generally rectilinear configuration. The eyelid contacting member fabric layer has a first edge, with the first edge having a generally arcuate configuration.

The fabric layer has an outer surface and an inner surface. The inner surface has a layer of a first adhesive. The first adhesive layer is overlayed with a removable cover, thereby containing the first adhesive between the inner surface of the fabric layer of the eyelid contacting member and the removable cover.

Next, there is a forehead contacting member. The forehead contacting member has a flexible fabric layer in a generally rectilinear configuration. The fabric layer has an outer surface and an inner surface. The inner surface has a layer of a first adhesive. The first adhesive layer is overlayed with a removable cover, thereby containing the first adhesive between the inner surface of the fabric layer of the forehead contacting member and the removable cover.

Lastly, there is a connecting member. The connecting member is fabricated of a elastomeric material. The connecting member has a generally elongated solid tubular configuration. The elastomeric material is coupled to the forehead contacting member by a second adhesive. The elastomeric material is also coupled to the eyelid contacting member by the second adhesive. The connecting member couples the forehead contacting member and the eyelid contacting member.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved eyelid lifting device which has all of the advantages of the prior art adhesive devices and none of the disadvantages.

It is another object of the present invention to provide a new and improved eyelid lifting device which may be easily and efficiently manufactured and marketed.

It is further object of the present invention to provide a new and improved eyelid lifting device which is of durable and reliable constructions.

An even further object of the present invention is to provide a new and improved eyelid lifting device which is susceptible of a low cost of manufacture with regard to both materials and labor, and which accordingly is then susceptible of low prices of sale to the consuming public, thereby making such eyelid lifting device economically available to the buying public.

Even still another object of the present invention is to provide a eyelid lifting device for lifting a user's eyelid.

Lastly, it is an object of the present invention to provide a new and improved eyelid lifting device, comprising an eyelid contacting member, and a forehead contacting member, and an elastomeric connecting member. The eyelid contacting member and the forehead contacting member each having an adhesive layer with a cover coupled thereto.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
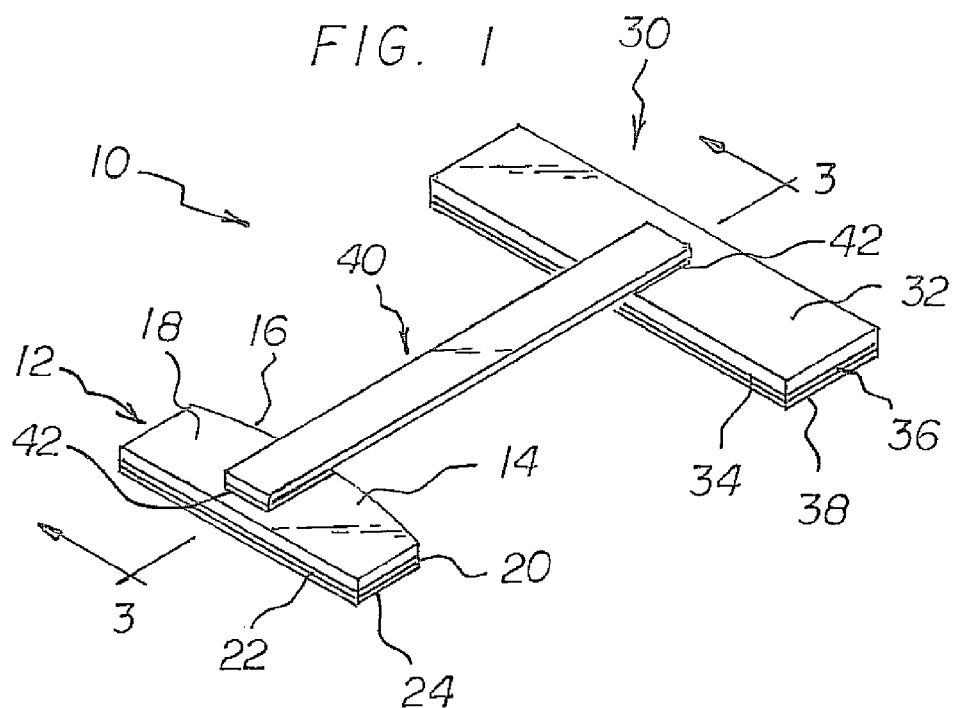
FIG. 1 is a top perspective view of the device.
Figure 2:
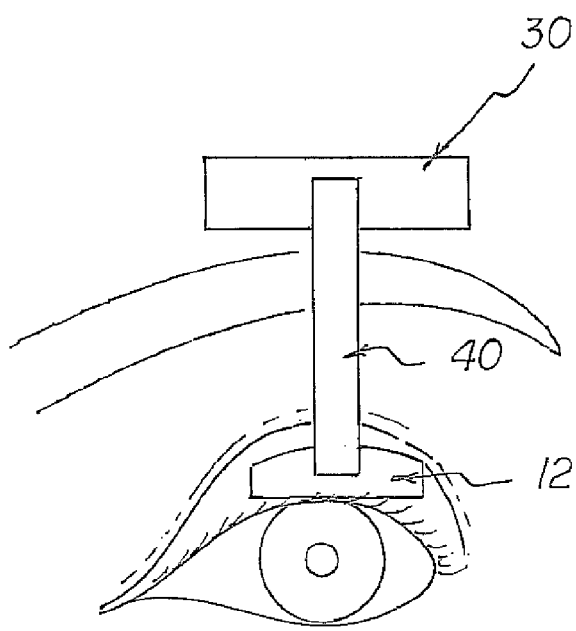
FIG. 2 is a view of the device when in use, showing the arcuate edge following the eye socket.
Figure 3:
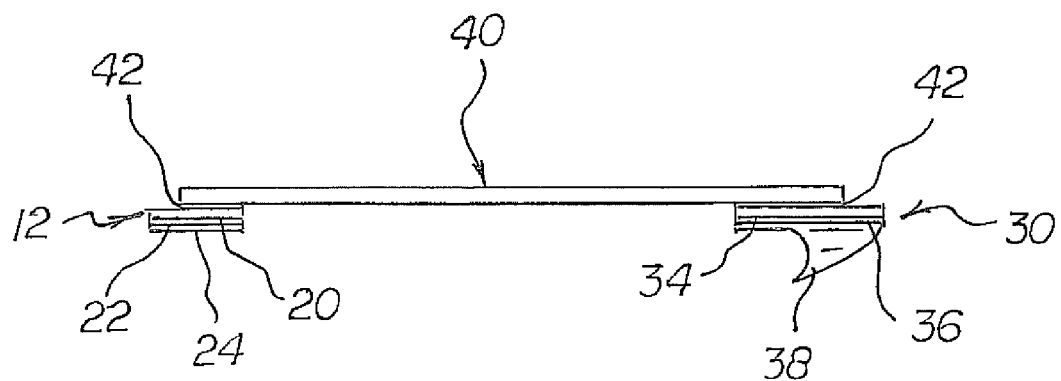
FIG. 3 is a view taken along line 3-3 of FIG. 1.
Figure 4:
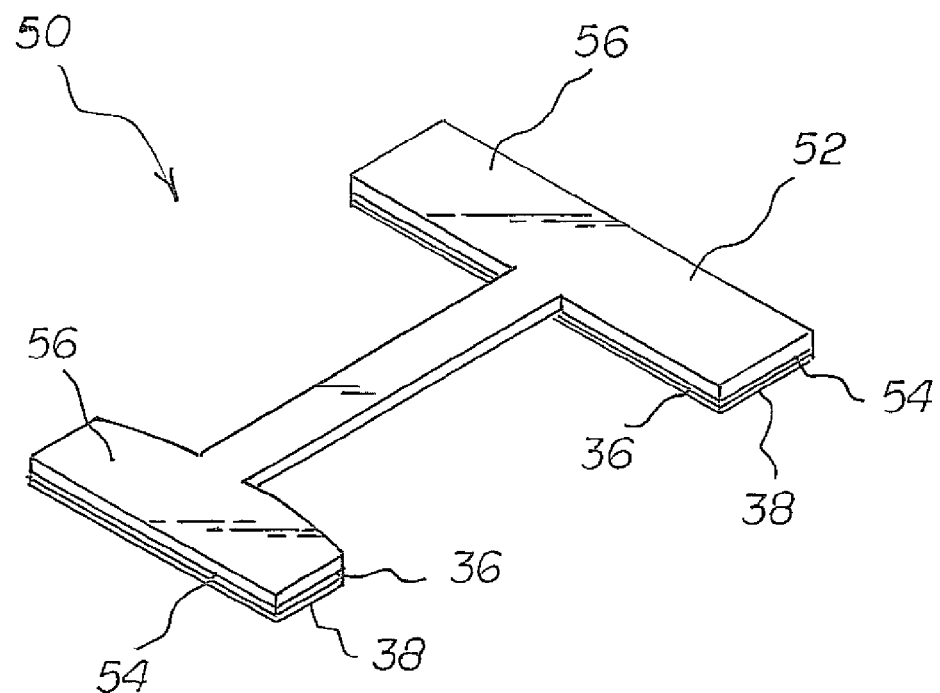
FIG. 4 is a top perspective view of a variation of the preferred embodiment, as when the device when made of a single elastomeric material.

With reference now to the drawings, and in particular to FIG. 1 thereof, the preferred embodiment of the new and improved eyelid lifting device embodying the principles and concepts of the present invention and generally designated by the reference numeral 10 will be described.

The present invention, the eyelid lifting device is comprised of a plurality of components. Such components in their broadest context include an eyelid contacting member, a forehead contacting member, a first adhesive and a cover. Such components are individually configured and correlated with respect to each other so as to attain the desired objective.

A eyelid lifting device 10, comprising several components, in combination.

First there is an eyelid contacting member 12. The eyelid contacting member has a flexible fabric layer 14. The flexible fabric layer is in a generally rectilinear configuration. The eyelid contacting member fabric layer has a first edge 16, with the first edge having a generally arcuate configuration. The eyelid contacting member has a first length and a first width and a first thickness, as shown in FIG. 1. The first, arcuate, edge 16 runs the width of the eyelid contacting member, also as shown in FIG. 1. The eyelid contacting member has an axis which runs its length.

The fabric layer has an outer surface 18 and an inner surface 20.

The inner surface of the eyelid contacting member has a layer of a first adhesive 22. The first adhesive layer is overlayed with a removable cover 24, thereby containing the first adhesive between the inner surface of the fabric layer of the eyelid contacting member and the removable cover.

Next, there is a forehead contacting member 30. The forehead contacting member has a flexible fabric layer in a generally rectilinear configuration. The fabric layer has an outer surface 32 and an inner surface 34. The inner surface has a layer of the first adhesive 36. The first adhesive layer is overlayed with a removable cover 38, thereby containing the first adhesive between the inner surface of the fabric layer of the forehead contacting member and the removable cover. The forehead contacting member has a second length and a second width and a second thickness, as shown in FIG. 1. The second width runs generally along the first width of the eyelid contacting member, also as shown in FIG. 1. The forehead contacting member has an axis which runs its length.

Lastly, there is a connecting member 40. The connecting member is fabricated of a elastomeric material. The connecting member has a generally elongated solid tubular configuration. The elastomeric material is coupled to the forehead contacting member by a second adhesive 42. The elastomeric material is also coupled to the eyelid contacting member by the second adhesive 42. The connecting member couples the forehead contacting member and the eyelid contacting member. The connecting member has a third length and a third width and a third thickness, as shown in FIG. 1. The third width runs generally along the first width of the eyelid contacting member, and the second width of the forehead contacting member, also as shown in FIG. 1. The first width is less than the second width and the third width is less than the first width. The first length is less than the second length, and the second length is less than the third length, all as shown in FIG. 1. The connecting member has an axis which lies transverse to the axes of the forehead contacting member and the eyelid contacting member.

In another configuration of the device 50, the eyelid contacting member and the forehead contacting member and the connecting member may all be fabricated of the same elastomeric material 52. The eyelid contacting member and the forehead contacting member each have an inner surface 54 and an outer surface 56.

A single first adhesive 36 is used to coat the inner surface of the eyelid contacting member and the inner surface of the forehead contacting member. A cover 38 is than placed over the first adhesive, to protect the adhesive prior to application. This configuration allows the manufacture to be made in a mold using a single elastomer, as well as a single adhesive. In this configuration, as in the primary embodiment, multiple devices may be provided on a single sheet of cover paper, with the user removing one device for each single use.

The fabric material used in fabricating the device is the same material used to make a commonly used product referred to as Breathe Right® Nasal Strips, manufactured by GlaxoSmithKline. The Breathe Right® strips also use the same adhesive on the inner surface of the eyelid contacting member and the forehead contacting member. The elastomeric connecting member is coupled to the eyelid contacting member and the forehead contacting member using a generally available commercial adhesive.

In use, the user first applies the eyelid contacting member, pulls up on the eyelid, until the eyelid is in proper position, and then the forehead contacting member is adhered to the forehead of the user.

There are several medical conditions which cause a persons eyelids to droop, and cover the eye. Blepharospasm is one such condition. The eyelid drooping restricts activities, and prevents the operating of a motor vehicle, among other visual related activities. Treatment of Blepharospasm, and such maladies, presently is carried out with injections, such as with Botulinum Toxin, or with surgery.

The present device is superior to the existing treatments, in that the device keeps the eye open, and the elastomeric member allows the user to close the lid at will, such as in "blinking". The small size of the device means that the device is relatively inconspicuous in use. The fabrication of a device using a single elastomeric material may allow the device to be manufacture is a "clear" state, further decreasing the visibility of the device, when in use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An eyelid lifting device, comprising, in combination:
   an eyelid contacting member having a first width and an eyelid contacting member long axis;
   a forehead contacting member having a second width and a forehead contacting member long axis;
   an elastomeric connecting member having a third width, with the elastomeric contacting member being coupled to an outer surface of the eyelid contacting member and the elastomeric connecting member being coupled to an outer surface of the forehead contacting member, the elastomeric connecting member thereby coupling the eyelid contacting member and the forehead contacting member, with the first width being less than the second width and the third width being less than the first width;
   the eyelid contacting member having an inner surface having a layer of a first adhesive coupled thereto;
   the forehead contacting member having an inner surface having a layer of a first adhesive coupled thereto;
   the elastomeric connecting member being coupled to the forehead contacting member by a second adhesive;
   the eyelid contacting member having a generally rectilinear configuration with an inner edge having an arcuate configuration;
   the forehead contacting member having a generally rectilinear configuration with an inner edge having a linear configuration; and
   the elastomeric connecting member having a generally elongated solid tubular configuration, the elastomeric connecting member having a long axis transverse to the long axes of the eyelid contact member and the forehead contact member.

2. The eyelid lifting device as described in claim 1, with the device further comprising:
   with the first adhesive layer of the eyelid contacting member being overlayed with a removable cover, thereby containing the first adhesive between the inner surface of the eyelid contacting member and the removable cover; and
   the first adhesive layer of the forehead contacting member being overlayed with a removable cover, thereby containing the first adhesive between the inner surface of the forehead contacting member and the removable cover.

3. The eyelid lifting device as described in claim 1, with the device further comprising the elastomer material being coupled to the eyelid contacting member by the second adhesive;
   the eyelid contacting member comprising a fabric layer with the fabric layer being flexible; and
   the forehead contacting member comprising a fabric layer with the fabric layer being flexible.

4. The eyelid lifting device as described in claim 1, with the device further comprising the first adhesive layer of the eyelid contacting member and the first adhesive layer of the forehead contacting member each being overlayed with a removable cover, thereby containing the first adhesive between the inner surface of the eyelid contacting member and the removable cover and thereby containing the first adhesive between the inner surface of the forehead contacting member and the removable cover.

5. A method of treating drooping eyelids comprising the steps of using a device comprising:
   an eyelid contacting member having a first width and an eyelid contacting member long axis;
   a forehead contacting member having a second width and a forehead contacting member long axis;
   and an elastomeric connecting member having a third width, with the elastomeric connecting member being coupled to the eyelid contacting member and the elastomeric connecting member being coupled to the forehead contacting member, the elastomeric connecting member thereby coupling the eyelid contacting member and the forehead contacting member, with the first width being less than the second width and the third width being less than the first width;
   the eyelid contacting member having an inner surface having a layer of a first adhesive coupled thereto;
   The forehead contacting member having an inner surface having a layer of the first adhesive coupled thereto;
   the elastomeric connecting member being coupled to the forehead contacting member by a second adhesive;
   the eyelid contacting member having a generally rectilinear configuration with an inner edge having an arcuate configuration and the elastomeric connecting member having a generally elongated solid tubular configuration, the elastomeric connecting member having a long axis transverse to the long axes of the eyelid contact member and the forehead contact member;
   a user having an eyelid and a forehead, with the user coupling the eyelid contact member to the user's eyelid; and
   the user coupling the forehead contact member to the user's forehead.

* * * * *